(12) United States Patent
Kuboi

(10) Patent No.: US 10,813,537 B2
(45) Date of Patent: Oct. 27, 2020

(54) SHAPE DETECTION DEVICE

(71) Applicant: OLYMPUS CORPORATION, Tokyo (JP)

(72) Inventor: Toru Kuboi, Machida (JP)

(73) Assignee: OLYMPUS CORPORATION, Tokyo (JP)

( * ) Notice: Subject to any disclaimer, the term of this patent is extended or adjusted under 35 U.S.C. 154(b) by 359 days.

(21) Appl. No.: 15/866,535

(22) Filed: Jan. 10, 2018

(65) Prior Publication Data

US 2018/0160882 A1     Jun. 14, 2018

Related U.S. Application Data

(63) Continuation of application No. PCT/JP2015/069933, filed on Jul. 10, 2015.

(51) Int. Cl.
*G01B 11/24* (2006.01)
*A61B 34/20* (2016.01)
(Continued)

(52) U.S. Cl.
CPC .......... *A61B 1/0051* (2013.01); *A61B 1/0011* (2013.01); *A61B 1/00071* (2013.01);
(Continued)

(58) Field of Classification Search
CPC combination set(s) only.
See application file for complete search history.

(56) References Cited

U.S. PATENT DOCUMENTS 5,840,024 A * 11/1998 Taniguchi ............ A61B 1/0051
                                                    600/424
6,127,672 A * 10/2000 Danisch ................. G01B 11/18
                                                  250/227.14
(Continued)

FOREIGN PATENT DOCUMENTS

CN     102103228 A     6/2011
CN     102196761 A     9/2011
(Continued)

OTHER PUBLICATIONS

International Search Report dated Oct. 6, 2015 issued in PCT/JP2015/069933.
(Continued)

*Primary Examiner* — John P Leubecker
*Assistant Examiner* — Shankar Raj Ghimire
(74) *Attorney, Agent, or Firm* — Scully, Scott, Murphy & Presser, P.C.

(57) ABSTRACT

A shape detection device includes a flexible insertion section, a curved-shape detection sensor and a flexible exterior tube member arranged in the insertion section. The sensor includes an optical fiber, one or more detecting parts to change characteristics of light propagated by the optical fiber in accordance with a curved shape of the optical fiber, and a light detector. The flexible exterior tube member is arranged in the insertion section to include at least part of the optical fiber, and configured to be curved into a similar shape to the curved shape of the insertion section. The curved-shape detection sensor is partly held and fixed to at least one of the exterior tube member and a distal hold member provided at the distal end of the insertion section.

24 Claims, 11 Drawing Sheets

(51) Int. Cl.
*A61B 1/005* (2006.01)
*A61B 1/00* (2006.01)
*G02B 6/06* (2006.01)
*G01B 11/16* (2006.01)
*G02B 23/24* (2006.01)
*A61B 90/30* (2016.01)
*A61B 90/00* (2016.01)
*A61B 1/06* (2006.01)

(52) U.S. Cl.
CPC ............ *G01B 11/16* (2013.01); *G01B 11/24* (2013.01); *G02B 6/06* (2013.01); *G02B 23/24* (2013.01); *A61B 1/0669* (2013.01); *A61B 2034/2061* (2016.02); *A61B 2090/306* (2016.02); *A61B 2090/309* (2016.02); *A61B 2090/3614* (2016.02)

(56) References Cited

U.S. PATENT DOCUMENTS

| | | | | |
|---|---|---|---|---|
| 6,563,107 | B2* | 5/2003 | Danisch | G01B 11/18 250/227.14 |
| 7,296,363 | B2* | 11/2007 | Danisch | G01P 15/125 33/556 |
| 7,440,661 | B2* | 10/2008 | Kobayashi | A61B 5/065 385/117 |
| 8,219,180 | B2* | 7/2012 | Cao | A61B 5/06 600/117 |
| 8,725,234 | B2* | 5/2014 | Cao | A61B 5/06 385/13 |
| 9,784,569 | B2* | 10/2017 | Froggatt | G01B 11/16 |
| 10,238,837 | B2 | 3/2019 | Duindam | A61M 25/0133 |
| 2002/0088931 | A1* | 7/2002 | Danisch | G01D 5/268 250/227.14 |
| 2002/0183592 | A1* | 12/2002 | Suzuki | A61B 1/00071 600/145 |
| 2004/0165810 | A1* | 8/2004 | Fujita | A61B 1/0055 385/12 |
| 2008/0192241 | A1* | 8/2008 | He | G02B 6/2852 356/73.1 |
| 2008/0212082 | A1* | 9/2008 | Froggatt | G01M 11/083 356/73.1 |
| 2008/0285909 | A1* | 11/2008 | Younge | A61B 5/1076 385/13 |
| 2009/0123111 | A1* | 5/2009 | Udd | A61B 5/06 385/13 |
| 2009/0208143 | A1* | 8/2009 | Yoon | A61B 1/0058 382/321 |
| 2009/0324161 | A1* | 12/2009 | Prisco | G01L 1/246 385/13 |
| 2011/0098533 | A1* | 4/2011 | Onoda | G02B 23/2476 600/117 |
| 2013/0096572 | A1* | 4/2013 | Donhowe | A61B 34/10 606/130 |
| 2014/0230562 | A1* | 8/2014 | Yamamoto | G02B 23/2476 73/800 |
| 2014/0328557 | A1* | 11/2014 | Sakai | A61B 1/00165 385/12 |
| 2015/0219445 | A1* | 8/2015 | Duncan | E21B 47/0006 250/227.14 |

FOREIGN PATENT DOCUMENTS

| | | |
|---|---|---|
| JP | H10-286221 A | 10/1998 |
| JP | 2001-169998 A | 6/2001 |
| JP | 2002-345730 A | 12/2002 |
| JP | 2003-052612 A | 2/2003 |
| JP | 2003-052614 A | 2/2003 |
| JP | 2003-102677 A | 4/2003 |
| JP | 2008230244 A * | 10/2008 |
| JP | 2015-116390 A | 6/2015 |
| WO | WO 2010/050526 A1 | 12/2002 |

OTHER PUBLICATIONS

Chinese Office Action dated Dec. 9, 2019 in Chinese Patent Application No. 201580082803.9.
Chinese Office Action dated Mar. 5, 2019 in Chinese Patent Application No. 201580082803.9.
Japanese Office Action dated Sep. 11, 2018 in Japanese Patent Application No. 2017-528017.
English translation of International Preliminary Report on Patentability dated Jan. 25, 2018 together with the Written Opinion received in related International Application No. PCT/JP2015/069933.
Chinese Office Action dated May 25, 2020 in Chinese Patent Application No. 201580082803.9.

* cited by examiner

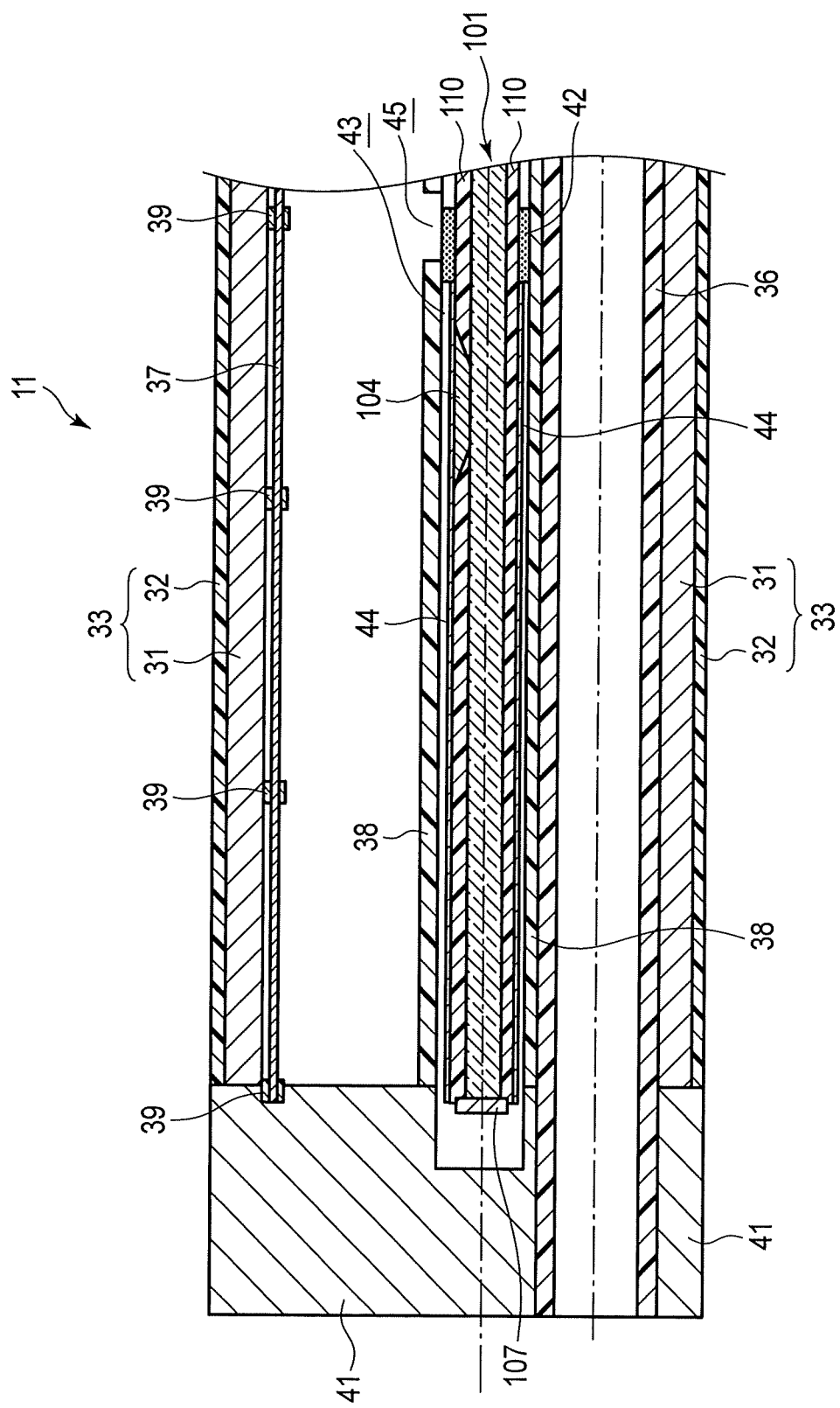
F I G. 5

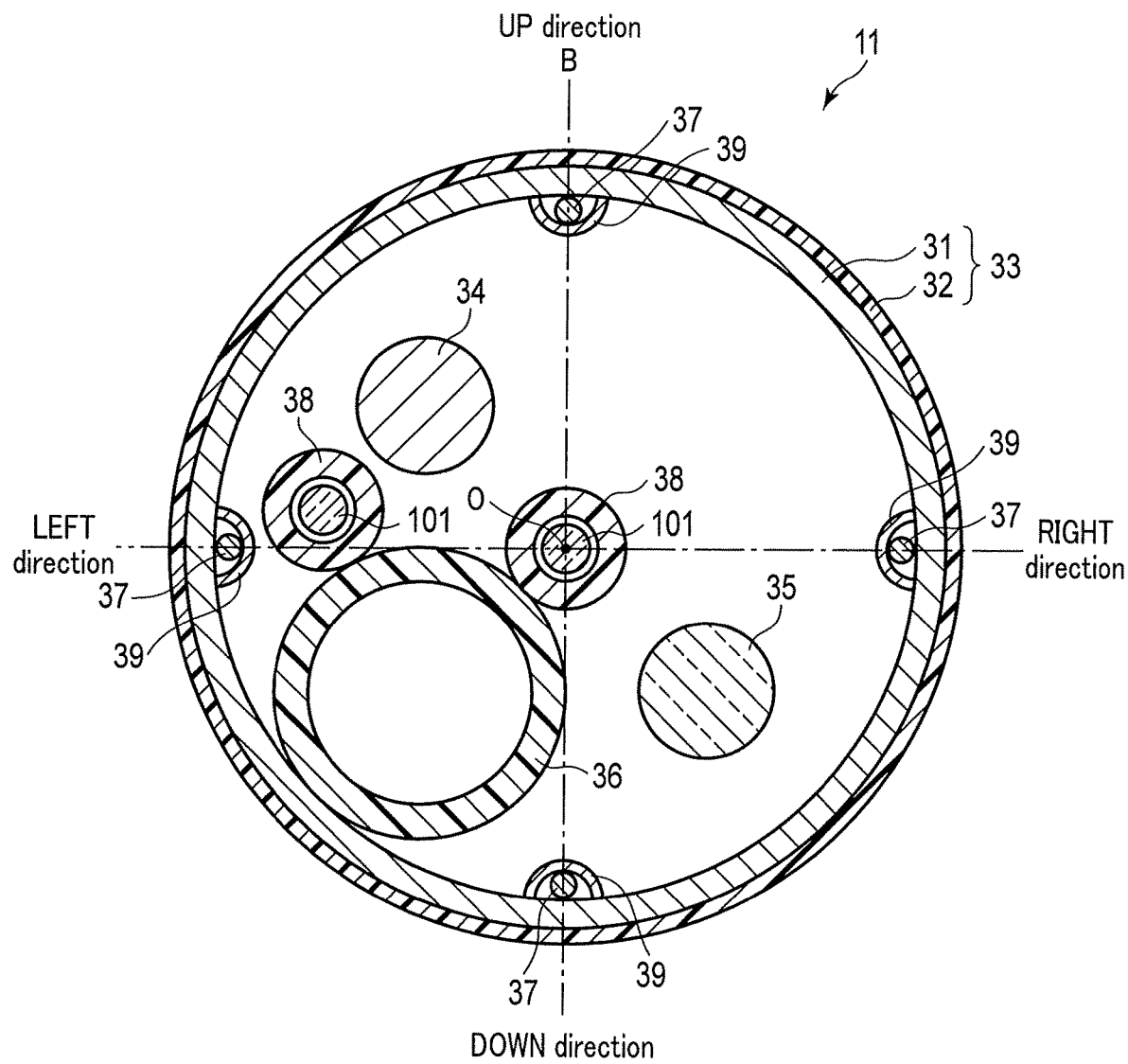
F I G. 6

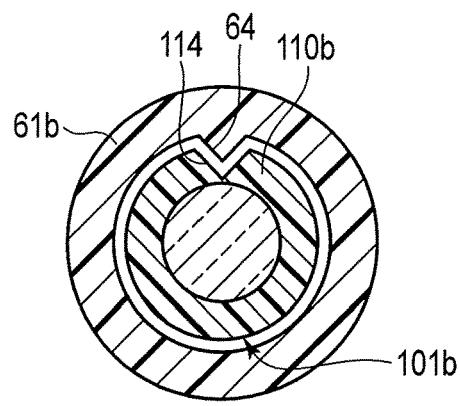
F I G. 11
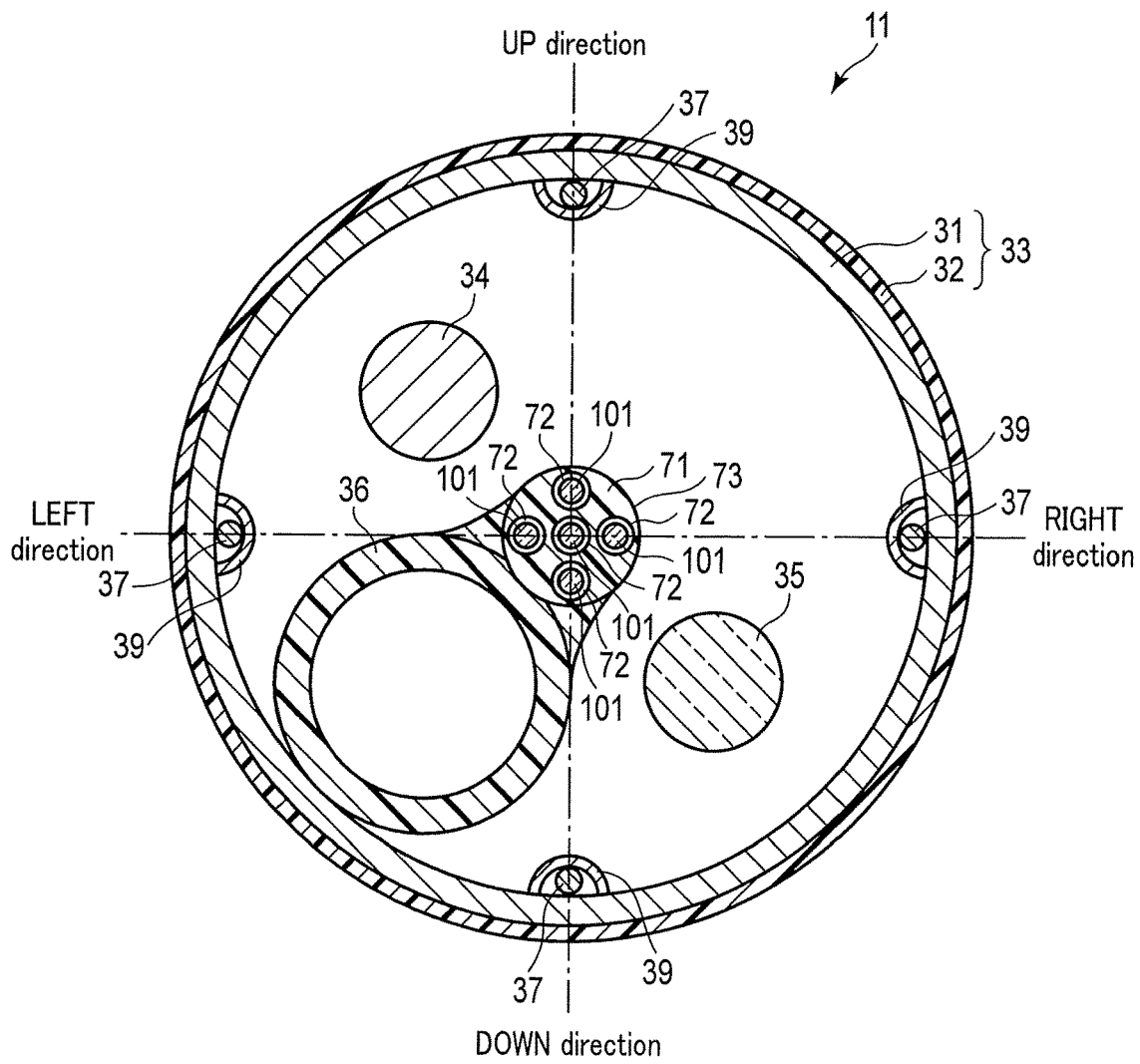
F I G. 12

SHAPE DETECTION DEVICE

CROSS-REFERENCE TO RELATED APPLICATIONS

This application is a Continuation Application of PCT Application No. PCT/JP2015/069933, filed Jul. 10, 2015, the entire contents of which are incorporated herein by reference.

BACKGROUND OF THE INVENTION

1. Field of the Invention

The present invention relates to a shape detection device comprising a curved-shape detection sensor capable of measuring a curved shape of an insertion section.

2. Description of the Related Art

In an insertion apparatus, such as an endoscope apparatus, which includes a flexible insertion section to be inserted in a subject, providing a curved-shape detection sensor in the insertion section to detect a curved shape of the insertion section is known. For example, Jpn. Pat. Appln. KOKAI Publication No. 2002-345730 discloses an endoscope apparatus in which a plurality of curve detection optical fibers each having a plurality of detecting parts and configured to change the light transmission amount in accordance with the angle of a curve are embedded in a tube wall of an insertion section in such a manner that the detecting parts are shifted in the axial direction of the insertion section. In this endoscope apparatus, curve states of the insertion section at positions of the detecting parts are detected based on the light transmission amounts of the curve detection optical fibers.

BRIEF SUMMARY OF THE INVENTION

One embodiment of the invention is a shape detection device comprising a flexible insertion section to be inserted in a subject, the insertion section including a distal end and a proximal end; a curved-shape detection sensor including an optical fiber arranged along a longitudinal direction of the insertion section and configured to propagate light output from a light source, one or more detecting parts arranged on a side surface of the optical fiber and configured to change characteristics of light propagated by the optical fiber in accordance with a curved shape of the optical fiber, and a light detector configured to detect light that has been propagated through the optical fiber via the detecting part; and a flexible exterior tube member arranged in the insertion section to include at least part of the optical fiber, having an inside diameter larger than an outside diameter of the optical fiber, and configured to be curved into a similar shape to the curved shape of the insertion section, wherein the curved-shape detection sensor is partly held and fixed to at least one of the exterior tube member and a distal hold member provided at the distal end of the insertion section.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute apart of the specification, illustrate embodiments of the invention, and together with the general description given above and the detailed description of the embodiments given below, serve to explain the principles of the invention.

FIG. 5 is a longitudinal cross-sectional view of the insertion section taken along line B-O-B in FIG. 4.

FIG. 6 is a radial cross-sectional view of the insertion section in the first embodiment.

FIG. 11 is a radial cross-sectional view of another example of the exterior tube member in the fourth embodiment.

FIG. 12 is a radial cross-sectional view of an example of the insertion section in the fifth embodiment.

DETAILED DESCRIPTION OF THE INVENTION

First Embodiment

An endoscope apparatus 1, which is a shape detection insertion apparatus, according to the first embodiment of the present invention includes a curved-shape detection sensor 101. First, the configuration and operation of the curved-shape detection sensor 101 will be described.

Figure 1:
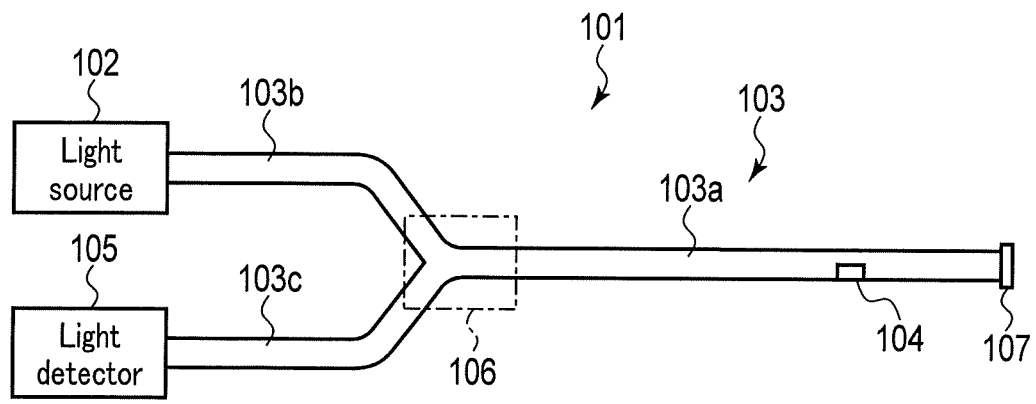
FIG. 1 is a schematic diagram illustrating principles of a curved-shape detection sensor.

FIG. 1 is a schematic diagram illustrating principles of the curved-shape detection sensor (hereinafter merely referred to as "sensor") 101. The sensor 101 includes a light source 102, an optical fiber 103, and a light detector 105. The optical fiber 103 is connected to the light source 102 and the light detector 105. The light source 102 is, for example, an LED light source or a laser light source, and outputs detection light having desired wavelength characteristics. The optical fiber 103 is an optical fiber for measuring a curved shape which propagates the detection light output from the light source 102. The light detector 105 detects the detection light propagated through the optical fiber 103.

The optical fiber 103 is flexible and includes a detection light optical fiber 103a, a light-supplying optical fiber 103b, and a light-receiving optical fiber 103c, which are three branches branching from a coupler (optical coupler) 106.

Namely, the optical fiber 103 is formed by connecting the light-supplying optical fiber 103b and the light-receiving fiber 103c to the detection light optical fiber 103a by the coupler 106. The proximal end of the light-supplying optical fiber 103b is connected to the light source 102. A reflector 107 for reflecting propagated light is provided at the distal end of the detection light optical fiber 103a. The reflector 107 is, for example, a mirror. The proximal end of the light-receiving optical fiber 103c is connected to the light detector 105.

The light-supplying optical fiber 103b propagates light output from the light source 102, and guides it to the coupler 106. The coupler 106 guides most of the light input from the light-supplying optical fiber 103b to the detection light optical fiber 103a, and guides at least part of the light reflected by the reflector 107 to the light-receiving optical fiber 103c. The light from the light-receiving optical fiber 103c is received by the light detector 105. The light detector 105 photoelectrically converts the received detection light, and outputs an electrical signal representing an amount of the detection light.

Figure 2:
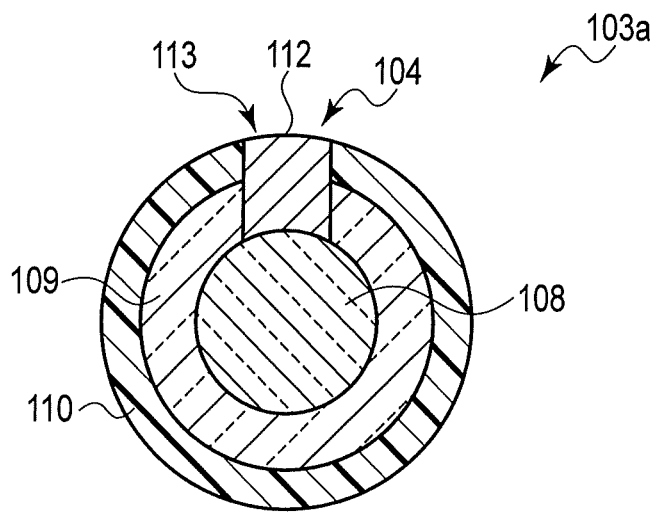
FIG. 2 is a radial cross-sectional view of the detection light optical fiber.

FIG. 2 is a radial cross-sectional view of the detection light optical fiber 103a. The detection light optical fiber 103a includes a core 108, a cladding 109 that covers the outer peripheral surface of the core 108, and a coating 110 that covers the outer peripheral surface of the cladding 109. At least one detecting part 104 is provided on a side surface of the detection light optical fiber 103a. The detecting part 104 is provided in only part of the outer periphery of the detection light optical fiber 103a, and changes the characteristics of the detection light that passes through the detecting part 104 in accordance with a change of the curved shape of the detection light optical fiber 103a.

The detecting section 104 includes an optical opening 112 formed by removing part of each of the cladding 109 and the coating 110 to expose the core 108, and an optical characteristic conversion member 113 formed in the optical opening 112. The optical opening 112 does not necessarily expose the core 108 as long as it allows light that passes through the detection light optical fiber 103a to reach the optical opening 112. The optical characteristic conversion member 113 converts the characteristics (such as an amount of light and a wavelength) of the light guided through the detection light optical fiber 103a, and is, for example, a guided light loss member (light absorber) or a wavelength conversion member (phosphor). In the following description, let us assume that the optical characteristic conversion member is a guided light loss member.

In the sensor 101, the light supplied from the light source 102 is propagated through the detection light optical fiber 103a as described above. When the light enters the optical characteristic conversion member 113 of the detecting part 104, part of the light is absorbed by the optical characteristic conversion member 113, which causes loss of guided light. The amount of this loss of guided light varies in accordance with the amount of curve of the detection light optical fiber 103a.

For example, even when the detection light optical fiber 103a is straight, a certain amount of light is lost in the optical characteristic conversion member 113 in accordance with the width, length, etc. of the optical opening 112. Let us assume that the amount of lost light in the straight state is a reference amount. When the optical characteristic conversion member 113 is provided on the outer side where the curvature radius is relatively large in a state where the detection light optical fiber 103a is curved, the amount of lost guided light is larger than the reference amount of lost guided light. When the optical characteristic conversion member 113 is provided on the inner side where the curvature radius is relatively small in a state where the detection light optical fiber 103a is curved, the amount of lost guided light is smaller than the reference amount of lost guided light.

The change in the amount of lost guided light is reflected in the amount of detection light received by the light detector 105, i.e., the output signal of the light detector 105. Accordingly, the curved shape at the position of the detecting part 104 of the sensor 101, i.e., the position where the optical characteristic conversion member 113 is provided, can be obtained based on the output signal of the light detector 105.

FIGS. 1 and 2 show only one detecting part 104; however, a plurality of detecting parts 104 may be provided in one detection light optical fiber 103a at intervals in the axial direction. This makes it possible to obtain a curved shape at a plurality of positions in the axial direction. Alternatively, two detecting parts 104 may be provided at approximately the same position in the axial direction and different positions (e.g., orthogonal positions) in the radial direction of one detection light optical fiber 103a. This makes it possible to obtain a curved shape in two directions orthogonal to each other. When a plurality of detecting parts 104 are provided in one detection light fiber 103a, the detection results at the detecting parts 104 are made distinguishable from each other by, for example, making different wavelengths lost by the optical characteristic conversion members 113.

The detection light optical fiber 103a of the sensor 101 is integrally attached to a long flexible curved target to be measured, which is the insertion section 11 of the endoscope 10 to be described later in the present embodiment, along the target. At the time of attachment, the sensor 101 is attached to a proper position of the insertion section 11 by adjusting a desired detection position of the insertion section 11 to the position of the detecting part 104 of the sensor 101. Then, the detection light optical fiber 103a is curved following the flexible movement of the insertion section 11, and the sensor 101 detects the curved shape of the insertion section 11 as described above. Namely, when the optical fiber 103 is curved, the sensor 101 detects the curved shape of the insertion section 11 by utilizing the fact that the characteristics of the detected light that has passed through the optical opening 112 change in accordance with the change in the curvature of the detection light optical fiber 103a.

Next, the configuration of the endoscope apparatus 1 will be described.

Figure 3:
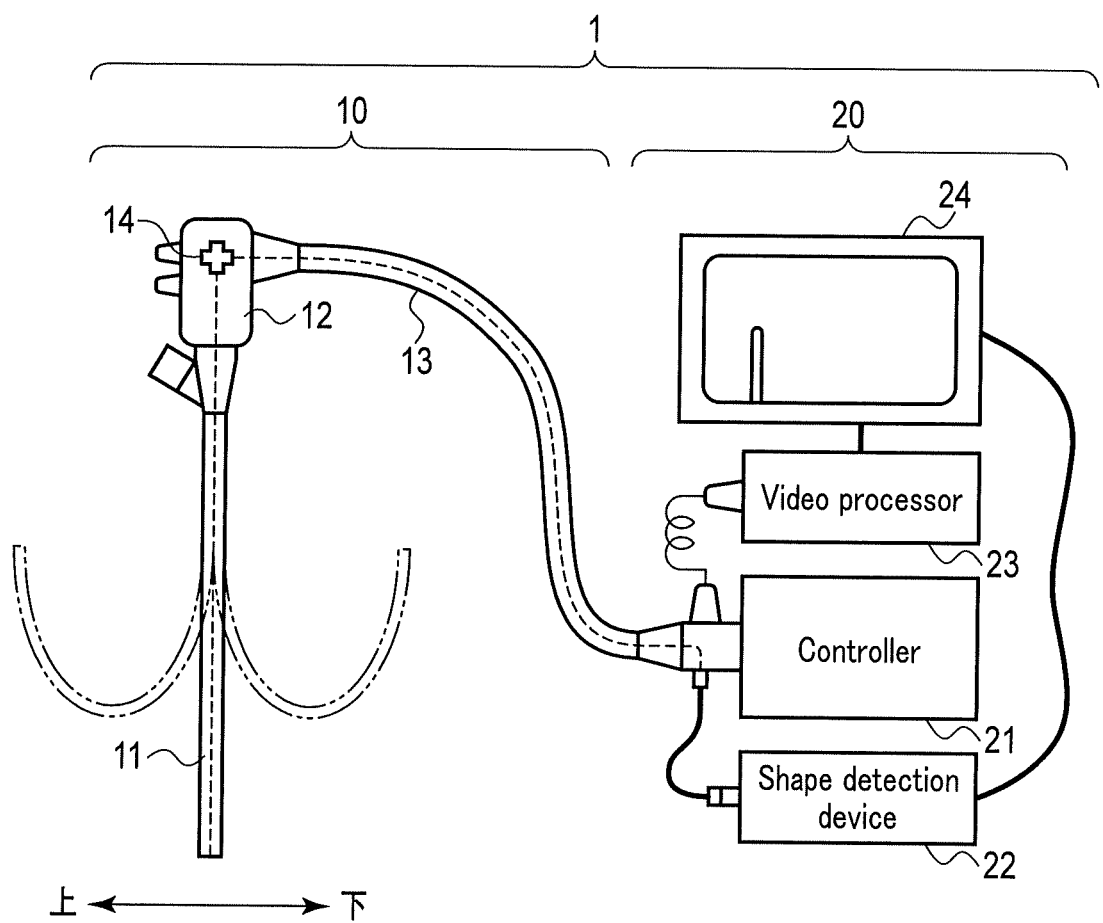
FIG. 3 schematically shows an endoscope apparatus including the curved-shape detection sensor.

FIG. 3 schematically shows the endoscope apparatus 1. The endoscope apparatus 1 includes an endoscope 10 containing therein at least the detection light optical fiber 103a of the sensor 101, and a main body 20. The main body 20 includes a controller 21, a shape detection device 22, a video processor 23, and a display 24. The controller 21 controls given functions of the endoscope 10, the shape detection device 22, and the video processor 23 as well as those of peripheral devices connected thereto. Although FIG. 3 does not show the sensor 101, the endoscope apparatus 1 includes the sensor 101 shown in FIG. 1. Namely, the endoscope apparatus 1 in the present embodiment is a shape detection insertion apparatus comprising a curved-shape detection sensor 101.

The endoscope 10 includes a flexible insertion section 11 to be inserted in a subject, and an operation section 12 provided proximal to the insertion section 11. A code section 13 extends from the operation section 12. The endoscope 10 is detachably connected to the main body 20 via the code section 13, and communicates with the main body 20. The operation section 12 includes an operation dial 14 for inputting an operation for curving the insertion section 11 in at least two specific directions (such as upward and downward) with a desired curvature. The code section 13 contains, for example, the camera cable 34 and light guide fiber 35 to be described later.

The endoscope apparatus 1 includes the sensor 101, and the detection light optical fiber 103*a* of the sensor 101 is provided in the insertion section 11. As described above, when the detection light optical fiber 103*a* is curved, the sensor 101 detects the curved shape of the insertion section 11 based on the change of the characteristics (amount of light in the present embodiment) of the detected light that has passed through the detecting part 104, which is made in accordance with the change in the curved shape.

The shape detection device 22 is connected to the light detector 105 of the sensor 101. The shape detection device 22 receives an output signal from the light detector 105, and calculates a curved shape of the insertion section 11 based on the output signal. The calculated curved shape is transmitted from the shape detection device 22 to the display 24 and is displayed on the display 24.

The video processor 23 performs image processing on an electrical signal obtained from an image pickup device (not shown) at the distal end of the endoscope via the camera cable 34 to be described later and the controller 21. The display 24 displays an image of the inside of a subject which is processed by the video processor 23.

Figure 4:
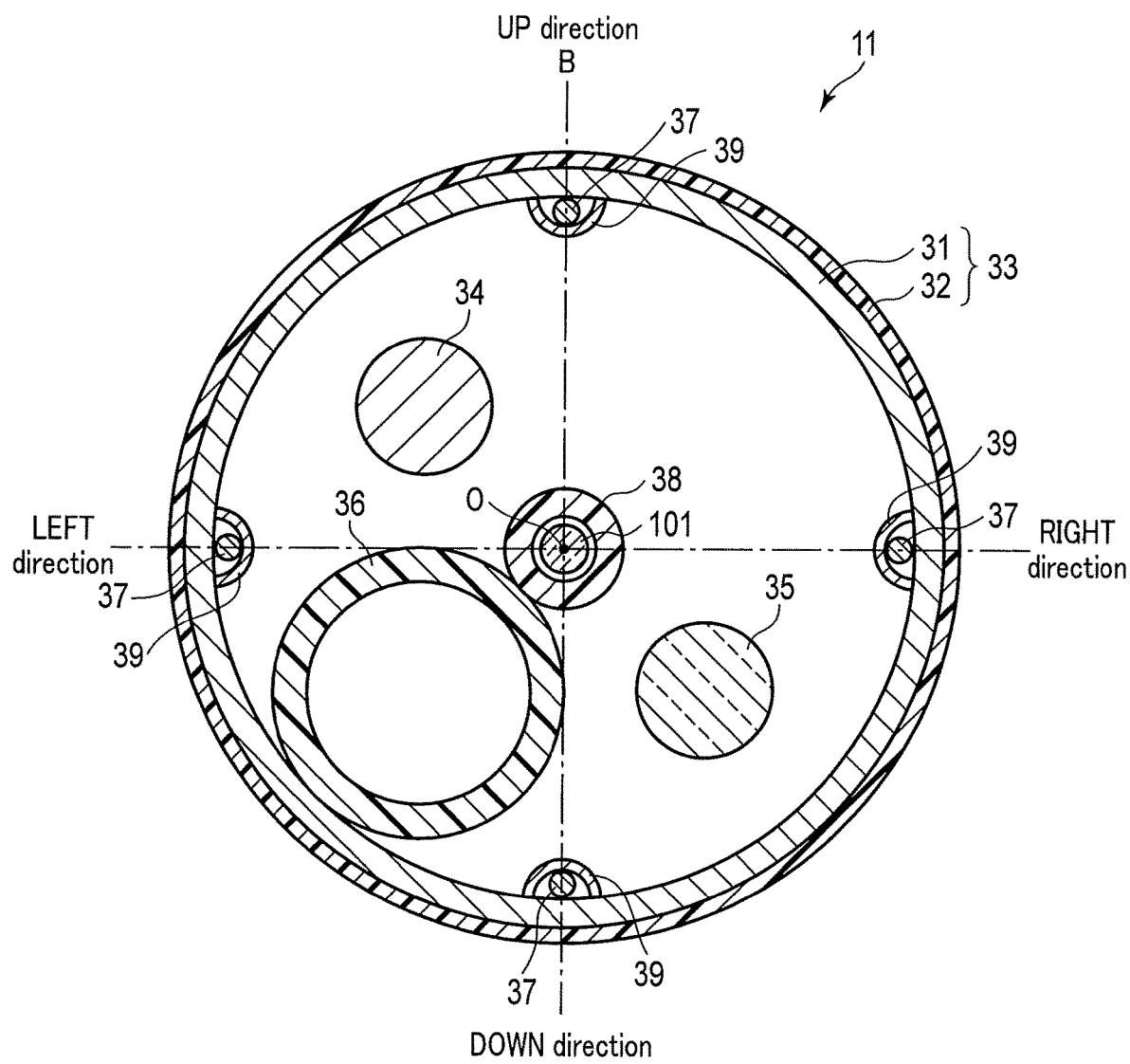
FIG. 4 is a radial cross-sectional view of an insertion section in the first embodiment.

FIG. 4 is a radial cross-sectional view of the insertion section 11 in the first embodiment. FIG. 5 is a longitudinal cross-sectional view of the insertion section 11 taken along line B-O-B in FIG. 4. Note that the scales of FIGS. 4 and 5 are not the same. The insertion section 11 is formed by containing, in a long hollow member 33 formed by covering the outer peripheral surface of a freely-curved long coil 31 with a flexible coating tube 32, a camera cable 34, a light guide fiber 35, a channel tube 36, a guide wire 37, and the detection light fiber 103*a* of the sensor 101 inserted in an exterior tube member 38.

The camera cable 34 is connected to the controller 21 and the image pickup device (not shown) at the distal end of the endoscope, and is electrical wiring for transmitting an electrical signal. The light guide fiber 35 is connected to an illumination section (not shown) at the distal end of the endoscope and to a light source (not shown) in the controller 21, and is a guide member that guides illumination light from the light source to the illumination section. The channel tube 36 is a cylindrical tube for allowing a treatment tool, such as an ultrasonic probe or a forceps, to be inserted therein.

The guide wire 37 is provided in the insertion section 11 along the axial direction to perform an operation of curving the insertion section 11 in a desired direction with a desired curvature. A wire receiver 39 having, for example, an approximately semicircular space is attached to the inner peripheral surface of the long coil 31, and the guide wire 37 is inserted in the space between the wire receiver 39 and the long coil 31. The distal end of the guide wire 37 is fixed to the distal end of the insertion section 11, and the proximal end of the guide wire 37 is coupled to the operation dial 14 of the operation section 12. When an operator operates the operation dial 14 to move the guide wire 37, the distal end of the insertion section 11 is curved.

In the present embodiment, as shown in FIG. 4, four guide wires 37 are provided for four directions (UP/DOWN/LEFT/RIGHT), respectively; therefore, four wire receivers 39 corresponding thereto are provided. For example, when the guide wire 37 of the UP direction is drawn by a rotation operation of the operation dial 14, the distal end of the insertion section 11 is curved upward, and when the guide wire 37 of the DOWN direction is drawn by a rotation operation of the operation dial 14, the distal end of the insertion section 11 is curved downward. In this way, the curve direction and curvature of the distal end of the insertion section 11 are controlled by drawing the guide wire 37 of each direction by a desired amount by a rotation of the operation dial 14.

As shown in FIG. 5, the distal end of the insertion section 11 is provided with a hard distal hold member 41 including, for example, an image pickup device and an illumination section, which are not shown. The distal hold member 41 holds at least the distal ends of the camera cable 34 and light guide fiber 35 (not shown in FIG. 5), the channel tube 36, and the guide wire 37 and exterior tube member 38.

The exterior tube member 38 is arranged at an approximate center in the radial direction of the long hollow member 33. For example, the central axis of the exterior tube member 38 approximately matches that of the long hollow member 33. The exterior tube member 38 includes at least part of the sensor 101, here, the detection light optical fiber 103*a*, and the detection light optical fiber 103*a* is also arranged at an approximate center in the radial direction of the insertion section 11 (long hollow member 33). The central axis of the sensor 101 (detection light optical fiber 103*a*) also approximately matches that of the insertion section 11 (long hollow member 33). The exterior tube member 38 is flexible, and a flexible tube of fluororesin base such as polytetrafluoroethylene (PTFE), or a tightly-wound metal coil (e.g., a stainless steel (SUS) spring) is suitable therefor.

The detection light fiber 103*a* of the sensor 101 is attached to the exterior tube member 38 by the outer peripheral surface of the coating 110 and the inner peripheral surface of the exterior tube member 38 being held and fixed by an elastic adhesive 42 only at one point located proximally with respect to the detecting part 104 in the axial direction (on the operation section 12 side of the endoscope 10) and in the vicinity of the detecting part 104. When a plurality of detecting parts 104 are provided in one detection light fiber 103*a*, the sensor 101 is attached to the exterior tube member 38 by being held and fixed at one point by the elastic adhesive 42 located proximally with respect to a detecting part 104 located most proximally among the detecting parts 104 and in the vicinity of that detecting part 104. In this way, the exterior tube member 38 restrains movement of at least part of the sensor 101, here, the detection light optical fiber 103*a*, by the holding and fixing only at one point.

The exterior tube member 38 is provided with a cutout opening 45 formed by cutting out part of the exterior tube member 38. The cutout opening 45 is formed in the vicinity of the position where the exterior tube member 38 is bonded to the sensor 101 by the elastic adhesive 42, i.e., the cutout opening 45 is located proximally with respect to the detecting part 104 and in the vicinity of the detecting part 104. The elastic adhesive 42 is supplied through the cutout opening 45, whereby the sensor 101 is held and fixed to the exterior tube member 38 only at one point.

At least one of the coating 110 of the detection light fiber 103*a* of the sensor 101 and the cutout opening 45 of the exterior tube member 38 is subjected to microwave plasma treatment. This treatment makes a surface modification of ethylene tetrafluoroethylene (ETFE) copolymer, which is a material of the coating 110 or the exterior tube member 38, and improves adhesiveness between the sensor 101 and the exterior tube member 38 for holding and fixing.

If the exterior tube member 38 is a fluororesin base tube, and the coating 110 of the detection light fiber 103*a* of the sensor 101 is the same fluororesin, the exterior tube member 38 and the sensor 101 may be held and fixed by fusion.

When the exterior tube member 38 is a tightly-wound coil (coil member), the cutout opening 45 may be not only a gap formed by cutting part of the exterior tube member 38, but also a gap formed by extending the coil in the axial direction for plastic deformation.

A moderate space 43 is formed between the exterior tube member 38 and the sensor 101 so that the sensor 101 can smoothly slide in the exterior tube member 38 in the axial direction. Namely, the inside diameter of the exterior tube member 38 is set to be larger than the outside diameter of the coating 110 of the detection light fiber 103*a* of the sensor 101. If necessary, the space 43 may be filled with a solid lubricant 44 such as molybdenum disulfide or carbon powder.

As shown in FIG. 6, the insertion section 11 may have a plurality of exterior tube members 38 each including the sensor 101 inserted thereinto. Even in this case, one exterior tube member 38 of the plurality of exterior tube members 38 is arranged at an approximate center in the radial direction of the insertion section 11 (long hollow member 33). Namely, the detection light optical fiber 103*a* of one sensor 101 is arranged at an approximate center in the radial direction of the insertion section 11 (long hollow member 33).

Next, the operation and advantage of curved shape detection of the endoscope apparatus 1 will be described. When the insertion section 11 of the endoscope 10 is curved by a rotation operation of the operation dial 14 or by being pressed in a subject, the exterior tube member 38 contained in the insertion section 11 is also curved into a similar shape to the insertion section 11. When the exterior tube member 38 is pushed, for example, by the adjacent channel tube 36 owing to the curve, and is moved from the approximate center of the insertion section 11, a bending stress (compression force or tension force) due to the curve is applied to the sensor 101. In the present embodiment, however, the sensor 101 is held and fixed to the exterior tube member 38 only at one point; therefore, the movement is not restrained in the exterior tube member 38 except for the held and fixed point. Namely, the sensor 101 is movable in the axial direction in the exterior tube member 38 except for the bonded point with the exterior tube member 38. Therefore, the sensor 101 does not receive a compression force or a tension force, and is curved together with the exterior tube member 38 into a similar shape to the insertion section 11, thereby enabling detection of the curved shape and curve direction of the insertion section 11.

Filling the solid lubricant 44 in the space 43 between the inner peripheral surface of the exterior tube member 38 and the coating 110 reduces the slide friction resistance caused therebetween.

In addition, the sensor 101 is held and fixed to the exterior tube member 38 at one point located proximally with respect to the detecting part 104 located most proximally in the axial direction and in the vicinity of that detecting part 104. Therefore, even if the optical fiber 103 is twisted at the part of the optical fiber 103 which is located proximally with respect to the held and fixed point, the twist is not transferred to the detecting part 104. Therefore, such a twist does not influence curved shape detection by the sensor 101.

As described above, the present embodiment can provide a shape detection insertion apparatus capable of correctly detecting the curved shape and curve direction of the insertion section 11. In particular, a shape detection insertion apparatus which receives less compression force or tension force at the curved-shape detection sensor 101, i.e., which has high reliability can be provided.

Hereinafter, the second to sixth embodiments of the present invention will be described. Hereinafter, the same structural members as those in the first embodiment are assigned with the same reference numerals, and descriptions thereof are omitted while describing only the part different from the first embodiment.

Second Embodiment

Figure 7:
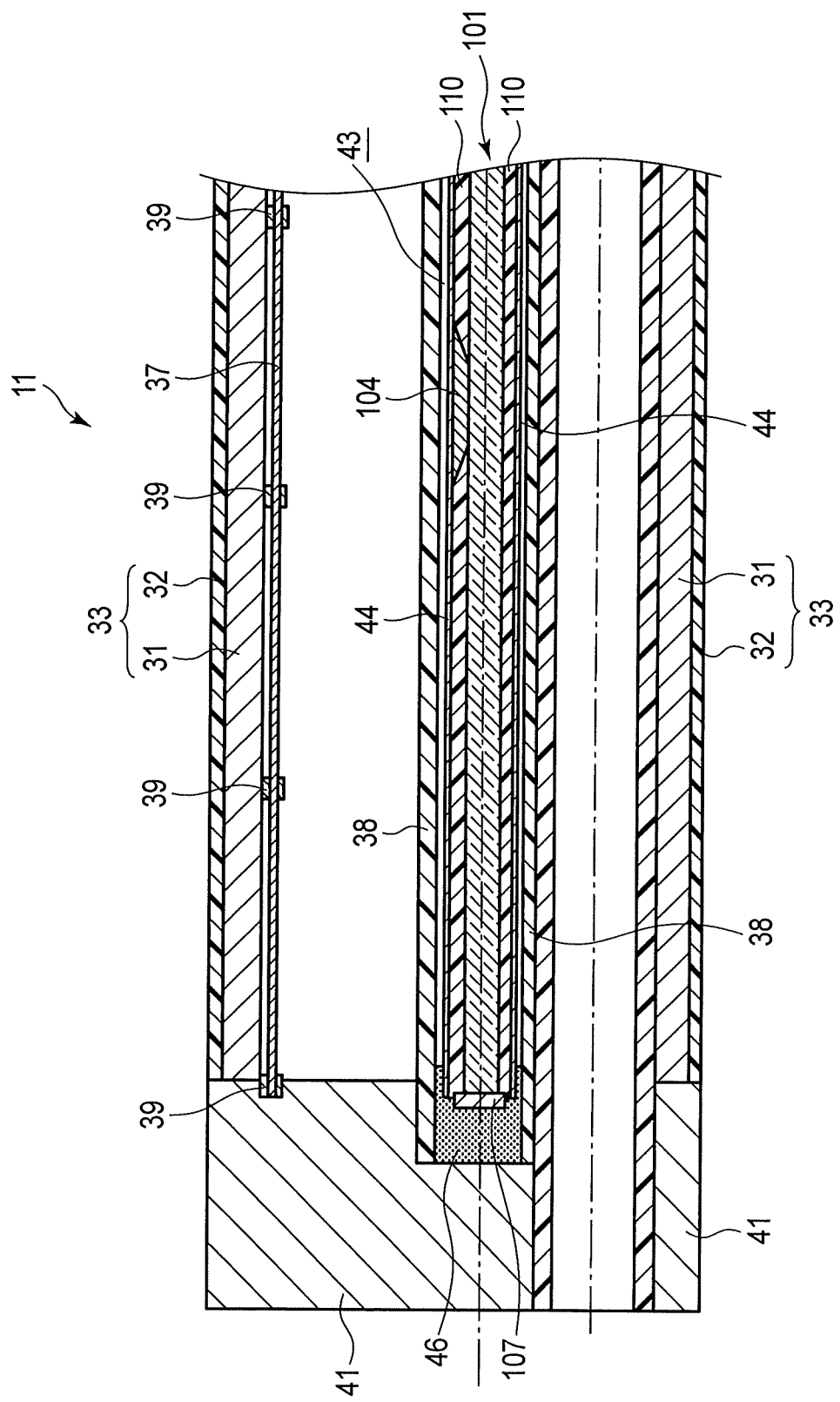
FIG. 7 is a longitudinal cross-sectional view of the insertion section corresponding to FIG. 5 in the second embodiment.

FIG. 7 is a longitudinal cross-sectional view of the insertion section 11 corresponding to FIG. 5 in the second embodiment. In the present embodiment, the sensor 101 is held and fixed by an adhesive 46 in the distal hold member 41 at only the distal end of the detection light fiber 103*a*. The adhesive 46 bonds the detection light fiber 103*a* of the sensor 101 to the exterior tube member 38, and the detection light fiber 103*a* of the sensor 101 to the distal hold member 41 in the neighborhood of the distal opening of the exterior tube member 38. Namely, in the present embodiment, the cutout opening 45 of the exterior tube member 38 in the first embodiment is not provided, and the elastic adhesive 42 that bonds the sensor 101 to the exterior tube member 38 located proximally with respect to the detecting part 104 is unnecessary. The adhesive 46 need not be an elastic adhesive as used in the first embodiment, and is preferably an epoxy-based adhesive or the like that is expected to have a higher adhesiveness. The sensor 101 (detection light optical fiber 103*a*) may be held and fixed by being bonded at its distal end only to the distal hold member 41 by the adhesive 46 as long as the sensor 101 is included in the exterior tube member 38 and movement of at least part of the sensor 101 is restrained.

In the present embodiment, the sensor 101 is held and fixed to the exterior tube member 38 only at its distal end; therefore, the movement is not restrained in the exterior tube member 38 except for the distal end. Namely, the sensor 101 is movable in the axial direction in the exterior tube member 38 except for the distal end. Therefore, even if the insertion section 11 is curved, the sensor 101 does not receive a compression force and a tension force, and the exterior tube member 38 and the sensor 101 are curved into a similar shape to the insertion section 11, thereby enabling detection of the curved shape and curve direction of the insertion section 11.

In addition, according to the present embodiment, the sensor 101 is bonded and fixed at the distal end of the exterior tube member 38; therefore, the cutout opening 45 need not be formed in the exterior tube member 38. The adhesive 46 can be supplied, for example, through the distal opening of the exterior tube member 38. Therefore, an adhesive can be supplied more easily than in the first embodiment.

The distal hold member 41 to which the sensor 101 is bonded is a hard portion including an image pickup device, an illumination section, etc., and is a non-curved member. This enables use of an adhesive 46 having a higher hardness and a higher adhesiveness (difficult to be bent).

Third Embodiment

Figure 8:
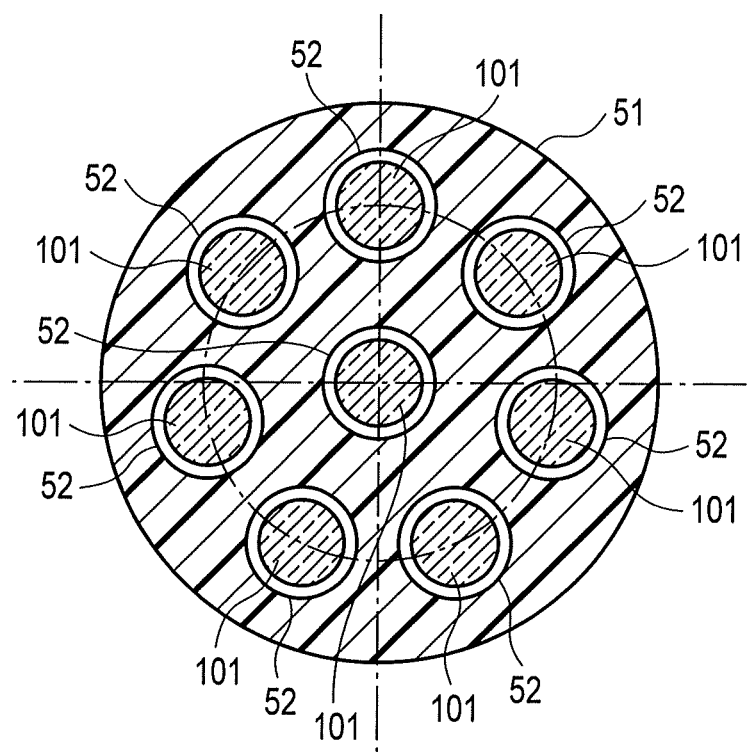
FIG. 8 is a radial cross-sectional view of an exterior tube member in the third embodiment.

FIG. 8 is a radial cross-sectional view of an exterior tube member 51 in the third embodiment. Shown here are only the exterior tube member 51 and the sensor 101 inserted thereto; however, this exterior tube member 51 is included in the long hollow member 33 of the insertion section 11 as in the first and second embodiments.

The exterior tube member 51 is a multi-lumen tube having at least two small lumens 52, which is independent (separated) from the other internal members (camera cable 34, light guide fiber 35, channel tube 36, etc.) in the insertion section 11. FIG. 8 shows, as an example, an exterior tube member 51 having eight small lumens 52. For example, one small lumen 52 of the small lumens 52 is at the center of the exterior tube member 51, and the other small lumens 52 are uniformly arranged on an arc around the one center small lumen 52. The number of small lumens 52 and the arrangement thereof are not limited to the above, and various numbers and arrangements are possible.

The sensor 101 is inserted in each of the small lumens 52. The outside shape of the radial cross section of each small lumen 52 is a circle, and the outside shape of the radial cross section of the coating 110 of the sensor 101 to be inserted is also a circle similar to the outside shape of the radial cross section of the small lumen 52. A space is formed between each small lumen 52 and sensor 101 as in the first embodiment so that the sensor 101 can smoothly slide in the small lumen 52 in the axial direction.

The exterior tube member 51 may be a bunch of a plurality of coils bonded by an adhesive or tied with a band. The sensor 101 may be bonded to the small lumen 52 located proximally with respect to the detecting part 104 and in the vicinity of the detecting part 104 as in the first embodiment, and may be bonded to the distal hold member 41 and the small lumen 52 at its distal end as in the second embodiment. For example, the sensor 101 inserted in the small lumen 52 at an approximate center of the exterior tube member 51 is held and fixed by at least one of the distal hold member 41 and the exterior tube member 51, and the sensor 101 inserted in the small lumen 52 at a position other than the approximate center is held and fixed by the exterior tube member 51 only at one point.

According to the present embodiment, providing a plurality of small lumens 52 in one exterior tube member 51 enables providing one exterior tube member 51 with detection light fibers 103a of a plurality of sensors 101. Therefore, if the detecting parts 104 of those sensors 101 are arranged at different positions in the axial direction, the detection points can be easily increased. Namely, it is possible to provide a shape detection insertion apparatus that can detect a curved shape and a curve direction of the insertion section 11 with high accuracy even when the insertion section 11 is long.

Fourth Embodiment

Figure 9:
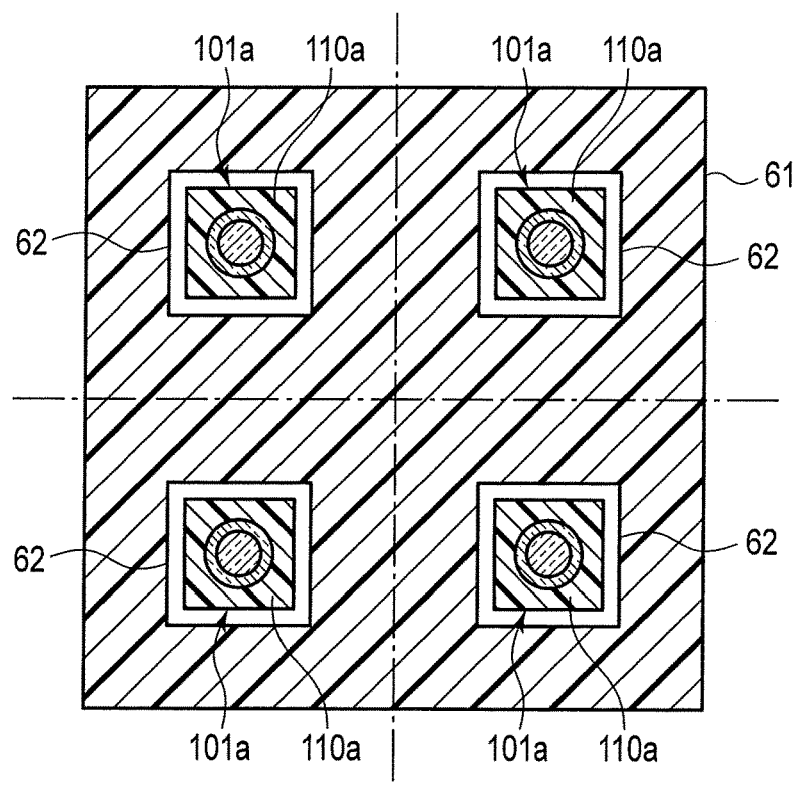
FIG. 9 is a radial cross-sectional view of an example of the exterior tube member in the fourth embodiment.

FIG. 9 is a radial cross-sectional view of an example of an exterior tube member 61 in the fourth embodiment. Shown here are only the exterior tube member 61 and the sensor 101a inserted thereto; however, this exterior tube member 61 is contained in the long hollow member 33 of the insertion section 11 as in the first and second embodiments.

In the present embodiment, the outside shape of the radial cross section of the exterior tube member 61 is non-circular (for example, triangular, rectangular, polygonal or oval). Hereinafter, an exterior tube member 61 having a square cross section will be described as an example.

The exterior tube member 61 includes four small lumens 62. Those small lumens 62 also have a square cross section. For example, four small lumens 62 are rotationally symmetric with respect to the center of the square of the cross section of the exterior tube member 61. However, the number of small lumens 62 and the arrangement thereof are not limited to the above, and various numbers and arrangements are possible. For example, the small lumens 62 may be provided at an approximate center of the radial cross section of the exterior tube member 61.

The detection light fiber 103aa of the sensor 101a is inserted in each of the small lumens 62. In the present embodiment, the outside shape of the radial cross section of the coating 110a of the sensor 101a inserted in each small lumen 62 is also a square similar to the outside shape of the radial cross section of the small lumen 62. A space is formed between the small lumen 62 and the sensor 101a as in the first embodiment so that the sensor 101a can smoothly slide in the small lumen 62 in the axial direction.

Figure 10:
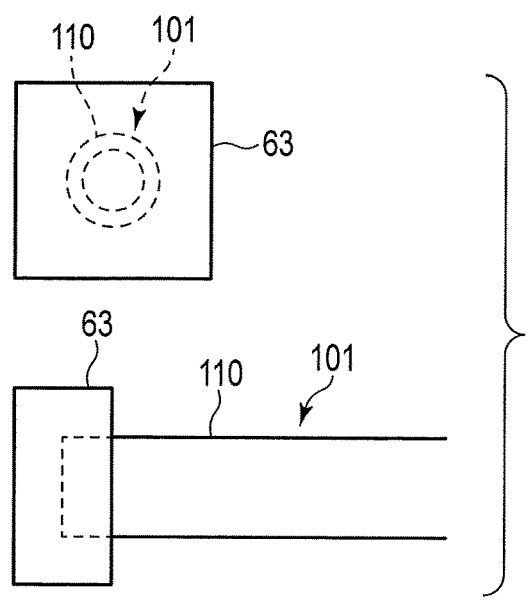
FIG. 10 is a front view and a side view showing an example of a cap member in the fourth embodiment.

Alternatively, as shown in FIG. 10, although the cross-section shape of the coating 110 of the detection light fiber 103a of the sensor 101 is circular, a cap member 63 capable of curving and having a cross-section shape similar to that of the small lumen 62 may be detachably attached to the distal end of the sensor 101. FIG. 10 shows a cap member 63 having a square cross section, which is attached to the circular coating 110 of the sensor 101 to be inserted in the small lumen 62 having a square cross section. The material of the cap member 63 is preferably the same as that of the coating 110, and is for example, ETFE.

The sensor 101a may be bonded to the small lumen 62 located proximally with respect to the detecting part 104 and in the vicinity of the detecting part 104 as in the first embodiment, and may be bonded to the distal hold member 41 and the small lumen 62 at its distal end as in the second embodiment. The same applies to the case where a cap member 63a is provided in the sensor 101.

FIG. 11 is a radial cross-sectional view of another example of the exterior tube member 61b in the fourth embodiment.

The exterior tube member 61b has a non-circular cross section having a protruding portion 64 on the inner surface. The coating 110b of the sensor 101b includes a depressed portion 114 corresponding to the protruding portion 64 of the exterior tube member 61b. At the time of insertion, registration is made so that the protruding portion 64 of the exterior tube member 61b fits in the depressed portion 114 of the coating 110b, whereby the sensor 101b is inserted in the exterior tube member 61b.

According to the present embodiment, even when a torque that tries to twist the exterior tube member 61 is produced by interference between the exterior tube member 61 and, for example, another internal member when the insertion section 11 is curved, the exterior tube member 61 resists twists because the outside radial cross section of the exterior tube member 61 is non-circular. Therefore, twists have little influence on the curved shape detection by the sensors 101a and 101b.

In addition, the sensor 101a not provided at the center of the insertion section 11 receives a bending stress when the insertion section 11 is curved, and the sensor 101a is held and fixed at only one point in the axial direction; therefore, the sensor 101a slides in the axial direction in the small lumen 62 of the exterior tube member 61 except for the held and fixed point when the insertion section 11 is curved. A torque that tries to twist the sensor 101a may be produced at the time of sliding; however, the sensor 101a resists twists in the small lumen 62 because the cross section of the coating 110a of the sensor 101a is non-circular in the present embodiment.

Moreover, when the sensor 101 has a coating 110 having a small diameter (approximately φ1 mm or less), making the cross section of the coating 110 non-circular may be difficult. In such a case, even when the cross section of the coating 110 is circular, the sensor 101 can be made resistant to twists by attaching the cap member 63 having a non-circular cross section to the distal end of the sensor 101.

According to the present embodiment, providing a plurality of small lumens 62 in one exterior tube member 61 enables providing one exterior tube member 61 with a plurality of sensors 101a. Accordingly, it is possible to increase the detection points, and provide a shape detection insertion apparatus that can detect a curved shape and a curve direction of the insertion section 11 with high accuracy even when the insertion section 11 is long.

Fifth Embodiment

FIG. 12 is a radial cross-sectional view of an example of the insertion section 11 in the fifth embodiment. The channel tube 36 is separate from the exterior tube member 38, 51 and 61 in the first to fourth embodiments, whereas the channel tube 36 is integrated with the exterior tube member 71 in the present embodiment. As in the exterior tube member 51 of the third embodiment, a plurality of small lumens 72 in which a plurality of sensors 101 are inserted respectively are formed in exterior tube member 71. FIG. 12 shows five small lumens 72 and five sensors 101 inserted thereto. At least one small lumen 72 of the exterior tube member 71 is formed in the protruding portion 73 provided outside the outer periphery of the channel tube 36. One small lumen 72 of the small lumens 72 is arranged at an approximate center in the radial direction of the insertion section 11. Namely, one sensor 101 of the sensors 101 inserted in the small lumens 72 is arranged at an approximate center in the radial direction of the insertion section 11.

Figure 13:
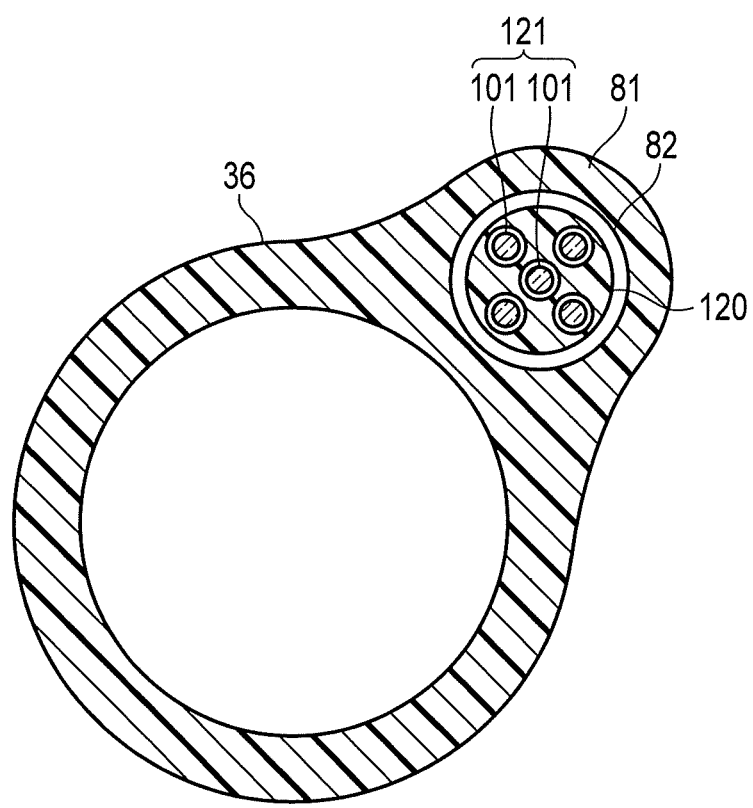
FIG. 13 is a radial cross-sectional view of the exterior tube member and channel tube of another example of the insertion section in the fifth embodiment.

FIG. 13 is a radial cross-sectional view of the exterior tube member 81 and channel tube 36 of another example of the insertion section 11 in the fifth embodiment. The channel tube 36 is integrated with the exterior tube member 81, and one lumen 82 is formed in the exterior tube member 81. Inserted in the lumen 82 is a sensor group 121 including a plurality of sensors 101 tied by a multi-lumen tube 120 like the exterior tube member 51 described in the third embodiment. Namely, a plurality of sensors 101 are inserted in one lumen 82.

Instead of integrating the channel tube 36 with the exterior tube member 71 and 81, the exterior tube member 71 and 81 may be held and fixed to the channel tube 36 with, for example, an elastic adhesive or band (not shown).

According to the present embodiment, the exterior tube member 71 and 81 is integrated with the channel tube 36 having high bending rigidity; therefore, the sensors 101 or the sensor group 121 inserted in the small lumens 72 or the lumen 82 of the exterior tube member 71 and 81 resists twists even when the insertion section 11 is curved. In addition, the exterior tube member 71 and 81 is not entangled in another inner part because it is integrated with the channel tube 36 having high bending rigidity. Accordingly, a shape detection insertion apparatus capable of higher-stability curved shape detection and having higher reliability than in the third and fourth embodiments can be provided. Furthermore, a shape detection insertion apparatus having higher reliability than in the first embodiment can be provided.

Sixth Embodiment

Figure 14:
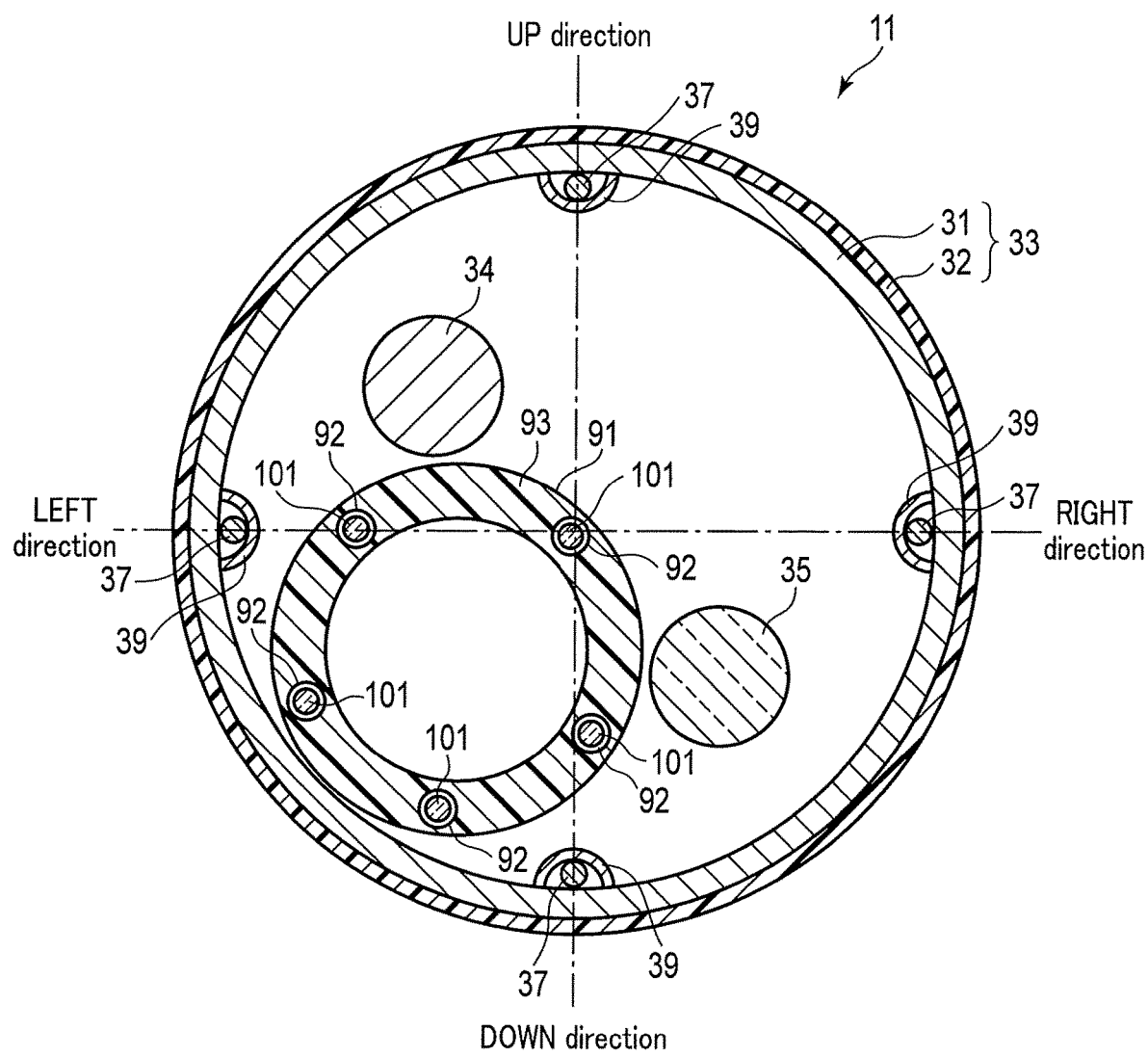
FIG. 14 is a radial cross-sectional view of the insertion section in the sixth embodiment.

FIG. 14 is a radial cross-sectional view of the insertion section 11 in the sixth embodiment. In the present embodiment, one or more small lumens 92 in which the sensor 101 is inserted are formed in a thick portion of the channel tube 91. Namely, in the present embodiment, although an independent exterior tube member is not provided in the long hollow member 33, the thick portion 93 of the channel tube 91 has the function of the exterior tube member. In FIG. 12, five small lumens 92 are uniformly arranged in the thick portion 93 of the channel tube 91, and the sensor 101 is inserted in each of the small lumens 92. One small lumen 92 of the small lumens 92 is arranged at an approximate center in the radial direction of the insertion section 11. Namely, one sensor 101 of the sensors 101 inserted in the small lumens 92 is arranged at an approximate center in the radial direction of the insertion section 11.

The small lumens 92 are not always formed in the channel tube 91, and may be formed in any other existing inner parts necessary for performing the functions as the endoscope 10 in the long hollow member 33 as long as the parts allow small lumens to be formed therein.

In the present embodiment, the cross-section shape of the channel tube 91 is approximately symmetric; therefore, the channel tube 91 can curve uniformly following the curved shape of the insertion section 11 regardless of in which direction the insertion section 11 curves. In addition, the protruding portion as described in the fifth embodiment is not formed on the outer periphery of the channel tube 91, which inhibits interference with another inner part, and decrease in the reliability of the sensor 101 due to the curve of the insertion section 11. Accordingly, a shape detection insertion apparatus capable of higher-stability curved shape detection and having higher reliability than in the third and fourth embodiments can be provided.

Various embodiments have been described above; however, the present invention is not limited to the embodiments described above, and various improvements and modifications can be made without departing from the subject matter of the present invention. For example, a person skilled in the art can conceive a shape detection insertion apparatus according to a combination of embodiments.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A shape detection device, comprising:
a flexible insertion section to be inserted in a subject, the insertion section including a distal end and a proximal end;
a curved-shape detection sensor comprising:
an optical fiber arranged along a longitudinal direction of the insertion section and configured to propagate light output from a light source,
one or more detecting parts arranged on a side surface of the optical fiber and configured to change characteristics of light propagated by the optical fiber in accordance with a curved shape of the optical fiber, and
a light detector configured to detect light that has been propagated through the optical fiber via the detecting part; and
a flexible exterior tube member arranged in the insertion section, at least part of the optical fiber being located inside the flexible exterior tube member, the flexible exterior tube member having an inside diameter larger than an outside diameter of the optical fiber, and configured to be curved into a similar shape to the curved shape of the insertion section,
wherein the optical fiber has a portion held and fixed to one of the exterior tube member and a distal hold member provided at the distal end of the insertion section;
the optical fiber is held and fixed by the exterior tube member only at one point;
the optical fiber comprises a plurality of optical fibers; and
a plurality of small lumens are formed in the exterior tube member and the optical fiber is inserted in each of the small lumens.

2. The shape detection device according to claim 1, wherein a distal end of the exterior tube member is held and fixed by the distal hold member.

3. The shape detection device according to claim 1, wherein the optical fiber is fixed and held by the exterior tube member only at the one point at a position located proximally with respect to the detecting part.

4. The shape detection device according to claim 1, wherein the plurality of optical fibers are provided with a plurality of detecting parts, and
the optical fiber is fixed and held by the exterior tube member only at the one point at a position located proximally with respect to a detecting part located most proximally among the detecting parts.

5. The shape detection device according to claim 1, wherein a distal end of the exterior tube member is held and fixed by the distal hold member, and
a distal end of the optical fiber is connected to the distal hold member and the distal end of the exterior tube member.

6. The shape detection device according to claim 1, wherein a distal end of the exterior tube member is held and fixed by the distal hold member, and
the optical fiber is fixed only to the distal hold member at a distal end of the optical fiber.

7. The shape detection device according to claim 1, wherein the optical fiber is positioned at an approximate center in a radial direction of the insertion section.

8. The shape detection device according to claim 1, wherein the exterior tube member is a resin tube.

9. The shape detection device according to claim 1, wherein the exterior tube member is a coil member.

10. The shape detection device according to claim 1, wherein the curved-shape detection sensor includes a coating member that covers the optical fiber, and
a solid lubricant is filled in a space formed between the exterior tube member and the coating member of the optical fiber inserted in the exterior tube member, thereby reducing a slide friction resistance produced between the exterior tube member and the coating member.

11. The shape detection device according to claim 1, wherein one small lumen of the small lumens is positioned at an approximate center in a radial direction of the insertion section.

12. The shape detection device according to claim 11, wherein an optical fiber inserted in the small lumen positioned at the approximate center is held and fixed by one of the distal hold member and the exterior tube member, and optical fibers other than the optical fiber inserted in the small lumen positioned at the approximate center are held and fixed by the exterior tube member only at one point.

13. The shape detection device according to claim 1, wherein the curved-shape detection sensor includes a coating member that covers the optical fiber, and
a radial cross section of the exterior tube member and that of the coating member are non-circular, and the optical fiber resists twists around a longitudinal axis in the exterior tube member.

14. The shape detection device according to claim 1, wherein the curved-shape detection sensor includes a coating member that covers the optical fiber, and
radial cross sections of the small lumens and that of the coating member are non-circular, and the optical fiber resists twists around a longitudinal axis in the exterior tube member.

15. The shape detection device according to claim 1, wherein a cap member having a non-circular cross section similar in shape to the radial cross sections of the small lumens and configured to be curved with a curvature equivalent to that of the insertion section is attached to the optical fiber.

16. The shape detection device according to claim 1, wherein the exterior tube member is an existing internal member in the insertion section.

17. The shape detection device according to claim 16, wherein the internal member is a channel tube, and the small lumens are provided in a thick portion of the channel tube.

18. The shape detection device according to claim 17, wherein the channel tube is integrated with the exterior tube member, and
the small lumens are provided in a protruding portion provided outside of an outer periphery of the channel tube.

19. The shape detection device according to claim 18, wherein one small lumen of the small lumens provided in the protruding portion is positioned at an approximate center in a radial direction of the insertion section.

20. The shape detection device according to claim 1, wherein the holding and fixing is performed by an elastic adhesive.

21. The shape detection device according to claim 20, wherein the curved-shape detection sensor includes a coating member that covers the optical fiber,
the exterior tube member includes a cutout opening, and
adhesiveness of at least one of the cutout opening and the coating member is improved by a surface modification using microwave plasma.

22. The shape detection device according to claim 21, wherein a material of the member on which the surface modification using microwave plasma is performed is ETFE.

23. The shape detection device according to claim 1, wherein the flexible insertion section includes an elongated hollow member, and
the flexible exterior tube member is separate from the elongated hollow member and arranged in the elongated hollow member to include at least part of the optical fiber.

24. A shape detection device, comprising:
a flexible insertion section to be inserted in a subject, the insertion section including a distal end and a proximal end;
a curved-shape detection sensor comprising:
an optical fiber arranged along a longitudinal direction of the insertion section and configured to propagate light output from a light source,
one or more detecting parts arranged on a side surface of the optical fiber and configured to change characteristics of light propagated by the optical fiber in accordance with a curved shape of the optical fiber, and a light detector configured to detect light that has been propagated through the optical fiber via the detecting part; and a flexible exterior tube member arranged in the insertion section, at least part of the optical fiber being located inside the flexible exterior tube member, the flexible exterior tube member having an inside diameter larger than an outside diameter of the optical fiber, and configured to be curved into a similar shape to the curved shape of the insertion section, wherein the optical fiber has a portion held and fixed to one of the exterior tube member and a distal hold member provided at the distal end of the insertion section;

the optical fiber is held and fixed by the exterior tube member only at one point;

the channel tube in the insertion section is integrated with the exterior tube member, and one lumen is formed in the exterior tube member, and the optical fiber inserted in the lumen is an optical fiber group tied by a multi-lumen tube including a plurality of small lumens in which a plurality of the optical fibers are inserted respectively.

\* \* \* \* \*